(12) United States Patent
Hibbs et al.

(10) Patent No.: US 10,068,490 B2
(45) Date of Patent: Sep. 4, 2018

(54) SYSTEM AND METHOD FOR IMPROVING STUDENT LEARNING BY MONITORING STUDENT COGNITIVE STATE

(71) Applicant: Quantum Applied Science and Research, Inc., San Diego, CA (US)

(72) Inventors: Andrew D. Hibbs, La Jolla, CA (US); Walid V. Soussou, San Diego, CA (US); Jason D. Jolly, Los Angeles, CA (US); Igor V. Fridman, San Diego, CA (US)

(73) Assignee: Quantum Applied Science and Research, Inc., San Diego, CA (US)

( * ) Notice: Subject to any disclaimer, the term of this patent is extended or adjusted under 35 U.S.C. 154(b) by 203 days.

(21) Appl. No.: 14/912,988

(22) PCT Filed: Aug. 21, 2014

(86) PCT No.: PCT/US2014/052126
§ 371 (c)(1),
(2) Date: Feb. 19, 2016

(87) PCT Pub. No.: WO2015/027079
PCT Pub. Date: Feb. 26, 2015

(65) Prior Publication Data
US 2016/0203726 A1    Jul. 14, 2016

Related U.S. Application Data

(60) Provisional application No. 61/868,270, filed on Aug. 21, 2013.

(51) Int. Cl.
*G09B 7/02*    (2006.01)
*A61B 3/113*    (2006.01)
(Continued)

(52) U.S. Cl.
CPC ............... *G09B 7/02* (2013.01); *A61B 3/113* (2013.01); *A61B 5/0205* (2013.01);
(Continued)

(58) Field of Classification Search
CPC .. G09B 7/02; G09B 5/06; A61B 3/113; A63B 5/0205; A63B 5/0402; A63B 5/0482; A63B 5/165; A63B 5/7267
See application file for complete search history.

(56) References Cited

U.S. PATENT DOCUMENTS 5,339,826 A * 8/1994 Schmidt ............. A61B 5/04842
600/544
5,724,987 A * 3/1998 Gevins ................. A61B 5/0484
600/544

(Continued)

*Primary Examiner* — Corbett B Coburn
(74) *Attorney, Agent, or Firm* — Diedericks & Whitelaw, PLC

(57) ABSTRACT

A system and method for improving student learning includes learning material that is presented to a student and a device that is used to acquire physiological data from the student in real time during a learning session. A cognitive assessment algorithm determines a cognitive state of the student using the physiological data, and a learning action algorithm modifies the presentation of the learning material in response to the student's cognitive state. The learning material can include lectures, questions asked of the student or problems or activities being completed by the student. In one embodiment, the device directly measures the brain activity of the student to determine the student's cognitive state. The cognitive state of the student can include the student's cognitive load, engagement or fatigue.

20 Claims, 2 Drawing Sheets

(51) Int. Cl.
*A61B 5/0205* (2006.01)
*A61B 5/0402* (2006.01)
*A61B 5/0482* (2006.01)
*A61B 5/16* (2006.01)
*A61B 5/00* (2006.01)
*G09B 5/06* (2006.01)
*A61B 5/024* (2006.01)
*A61B 5/053* (2006.01)

(52) U.S. Cl.
CPC .......... *A61B 5/0402* (2013.01); *A61B 5/0482* (2013.01); *A61B 5/165* (2013.01); *A61B 5/7267* (2013.01); *G09B 5/06* (2013.01); *A61B 5/02405* (2013.01); *A61B 5/0533* (2013.01)

(56) References Cited

U.S. PATENT DOCUMENTS

| | | | | |
|---|---|---|---|---|
| 8,271,077 B1* | 9/2012 | Rotenberg | ........... | A61B 5/0482 600/301 |
| 2003/0129574 A1* | 7/2003 | Ferriol | ..................... | G09B 5/00 434/362 |
| 2007/0184420 A1* | 8/2007 | Mathan | .................. | G09B 19/00 434/236 |
| 2008/0286737 A1 | 11/2008 | Cheng et al. | | |
| 2010/0292545 A1* | 11/2010 | Berka | ..................... | A61B 5/048 600/301 |
| 2011/0066005 A1* | 3/2011 | Rotenberg | ......... | A61B 5/02405 600/301 |
| 2011/0159467 A1* | 6/2011 | Peot | ....................... | A61B 3/113 434/157 |
| 2012/0052476 A1* | 3/2012 | Graesser | ................ | G09B 7/04 434/362 |
| 2014/0170626 A1 | 6/2014 | Lovett et al. | | |
| 2014/0212854 A1* | 7/2014 | Divakaran | ............ | G09B 19/00 434/236 |
| 2016/0242699 A1* | 8/2016 | Das | ...................... | A61B 5/0476 |
| 2016/0287157 A1* | 10/2016 | Simpson | ............... | A61B 5/168 |
| 2017/0249855 A1* | 8/2017 | Gazzaley | .............. | G09B 19/00 |
| 2017/0330475 A1* | 11/2017 | Minoda | ................ | A61B 5/0484 |

* cited by examiner

SYSTEM AND METHOD FOR IMPROVING STUDENT LEARNING BY MONITORING STUDENT COGNITIVE STATE

CROSS-REFERENCE TO RELATED APPLICATION

This application represents the U.S. National Stage of International Application No. PCT/GB2014/052126, filed 21 Aug. 2014 which claims the benefit of U.S. Provisional Patent Application Ser. No. 61/868,270, filed on Aug. 21, 2013. The entire content of these applications are incorporated herein by reference.

BACKGROUND OF THE INVENTION

The present invention relates to systems and methods for controlling the presentation of learning materials to a student. More particularly, the invention relates to monitoring a cognitive state of the student during a learning session and using this information to set a level of difficulty of the content, range of the content, rate of delivery of the content or level of interactivity during the learning session in order to improve the student's learning of the material. Yet more particularly, the invention is used during the lecturing or scaffolding phases of learning where conventional student assessment methods would interrupt the cooperation between the student and a tutor. This invention also encompasses using the student's cognitive states, and information derived from them, to develop individualized learning models and perform long-term data tracking and analysis.

The embodiments described herein relate generally to tutoring, wherein a human- or computer-based teacher presents material to a student for purposes of learning the material. As used herein, "student" generally refers to any person who is being taught and can be of any age. Similarly, the material to be learned is not restricted in any way and can be any material presented to a child in a K-12 classroom or at home or to an adult in a classroom or on the job.

Human tutors make decisions regarding what learning content to present, what order in which to present this content and whether and when to repeat parts or all of a specific unit of content. In addition, a tutor can choose to give feedback and hints to guide or help a student. One hypothesis about human tutors is that they infer an accurate model of a student's competence and misunderstandings and use this diagnostic assessment to adapt their tutoring to the needs of the individual student. However, studies show that while human tutors generally know which material a student has mastered, they rarely know the student's misconceptions, erroneous beliefs and problematic skills. Further, studies have shown that even if human tutors accurately know a student's misconceptions and false beliefs, they do not seem to be able to effectively use this information to improve learning outcomes.

Assessments can be made to infer student mastery and correct beliefs. Usually these assessments are made in light of a student's response to a specific question or steps taken in solving a question. Accordingly, the learning content of a student will typically be interspersed with regular sets of testing or assessment. This testing has two consequences: a) it interrupts the flow of the learning material, and b) it slows the progress of the able students and potentially over-challenges and demotivates the less able students. Further, such an assessment must always be done after the learning period and thus, even if the assessment is correct, it must be updated retroactively.

Learning itself is typically comprised of four stages: evaluation, lecturing, scaffolding and assessment. Feedback from the tutor to the student can be applied throughout the learning session to enable the student to find flaws in their reasoning and knowledge. Further, scaffolding by its very nature involves guided prompts and hints to extend a student's own line of reasoning to increase their level of understanding. Thus, a key part of learning is for the tutor to decide when to offer guidance back to the student. However, doing so requires an accurate assessment of the state of the student.

Rather than attempt to project the particular state of an individual student throughout a learning session, adaptive teaching platforms aim to categorize a student's responses against a series of metrics based upon the cumulative performance of other students and then deliver the content based on these metrics. However, even if the student is perfectly categorized so that the optimum learning content can be delivered, day to day variability due to fatigue, emotional state and consumption of neuroactive agents such as coffee, alcohol or nicotine can render such categorization temporarily erroneous and affect the accuracy of a subsequent categorization.

A cognitive gauge can provide a near real-time quantification of the cognitive state of a human subject. Inputs to cognitive gauges range from a time interval between successive actions and responses by the subject to facial recognition methods that assess confusion, frustration and boredom to direct measurements of the physiological activity of the brain. Gauges for cognitive workload, engagement, fatigue and executive function have been developed. Cognitive gauges have mostly been used for the objective quantification of the effect of complex tasks on workers. Potential applications investigated to date have focused on the control of high value assets, such as aircraft and critical systems, and air traffic control management.

A significant potential value of cognitive gauges in teaching is that they can monitor aspects of the cognitive state of the student during, rather than merely upon completion of, the presentation of key learning content. However, while information has, in some instances, been gathered throughout a learning session, previously this information has only been used after a learning session is finished for use in adapting subsequent learning sessions. When used in this delayed mode, such cognitive information is only an adjunct to test results, self-reporting by the student and other measures of learning outcome. As a result, it has only incremental value over more established and cheaper methods.

Once a system with real-time, continuous adaptation of the material and methods using feedback based on a student's cognitive states is employed, this information can be used to create a new, or complement an existing, learning model for each student. Learning models are currently used by companies specializing in "big data" in an effort to understand how each student best learns to improve overall student learning outcomes. "Big data" is a term for a collection of data sets so large and complex that it is difficult to process using traditional data processing techniques. Some examples of big data inputs include the traditional adaptive learning platform metrics such as response accuracy, response time and the student's confidence in their response, but big data efforts are increasingly looking to other metrics that schools have access to, including student demographic data, census information, city and state records, etc. Most of these inputs, however, rely on the assumption that a specific student learns in a similar fashion as other students. Using cognitive state information and, specifically, how a student responds to different teaching methods guided by these cognitive state measurements, as an input into a learning model can further and more accurately personalize the teaching experience to each student to improve their learning outcomes.

What is needed is a system and method that can monitor in real-time the cognitive response of a student during the learning activity and can use this information to adapt and modify the content and delivery methods to improve the student's ability to learn, updating if desired a predictive model of the student's learning. Such a system and method would have immediate benefit to human tutors by reporting student's state during learning and suggesting specific changes to the teaching content and approach. For computerized tutors, it would enable individualized closed-loop control of teaching material and its presentation.

SUMMARY OF THE INVENTION

The present invention is directed to a system and method for improving student learning. Learning material is presented to a student and a device is used to acquire physiological data from the student in real time during a learning session. A cognitive assessment algorithm determines a cognitive state of the student using the physiological data, and a learning action algorithm modifies the presentation of the learning material in response to the student's cognitive state. The learning material can include lectures, questions asked of the student, or problems or activities being completed by the student. In one embodiment, the device directly measures the brain activity of the student to determine the student's cognitive state. The cognitive assessment algorithm can also use a response time of the student or a quantification of a difficulty of a task in order to determine the student's cognitive state. The cognitive state of the student can include the student's cognitive load, engagement, fatigue, attention, boredom, arousal, frustration, or other mental or emotional states.

In addition to the student's cognitive state, the learning action algorithm can use information regarding whether the student correctly answered a question or completed a task in order to modify the presentation of the learning material. Preferably, the learning action algorithm modifies the presentation of the learning material during a lecturing or scaffolding phase of the learning session. Modifying the presentation of the learning material can include: changing the difficulty or interactivity of subsequent content; providing feedback to the student; changing the complexity or rate of delivery of the learning material; providing phrases to praise, motivate, admonish or engage the student; allowing the student to choose additional or alternative content; providing a prompt to induce the student to consider the student's reasoning; or adding additional tasks, removing tasks, changing the order of tasks or modifying tasks.

In one embodiment, the learning action algorithm updates a model that describes how the student learns. In another embodiment, a computer system includes a display for displaying the learning material to the student and, optionally, an input device for receiving input from the student.

Additional objects, features and advantages of the present invention will become more readily apparent from the following detail description of preferred embodiments when taken in conjunction with the drawings wherein like reference numerals refer to corresponding parts in the several views.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. Therefore, specific structural and functional details disclosed herein are not to be interpreted as limiting, but merely as a representative basis for teaching one skilled in the art to variously employ the present invention.

Figure 1:
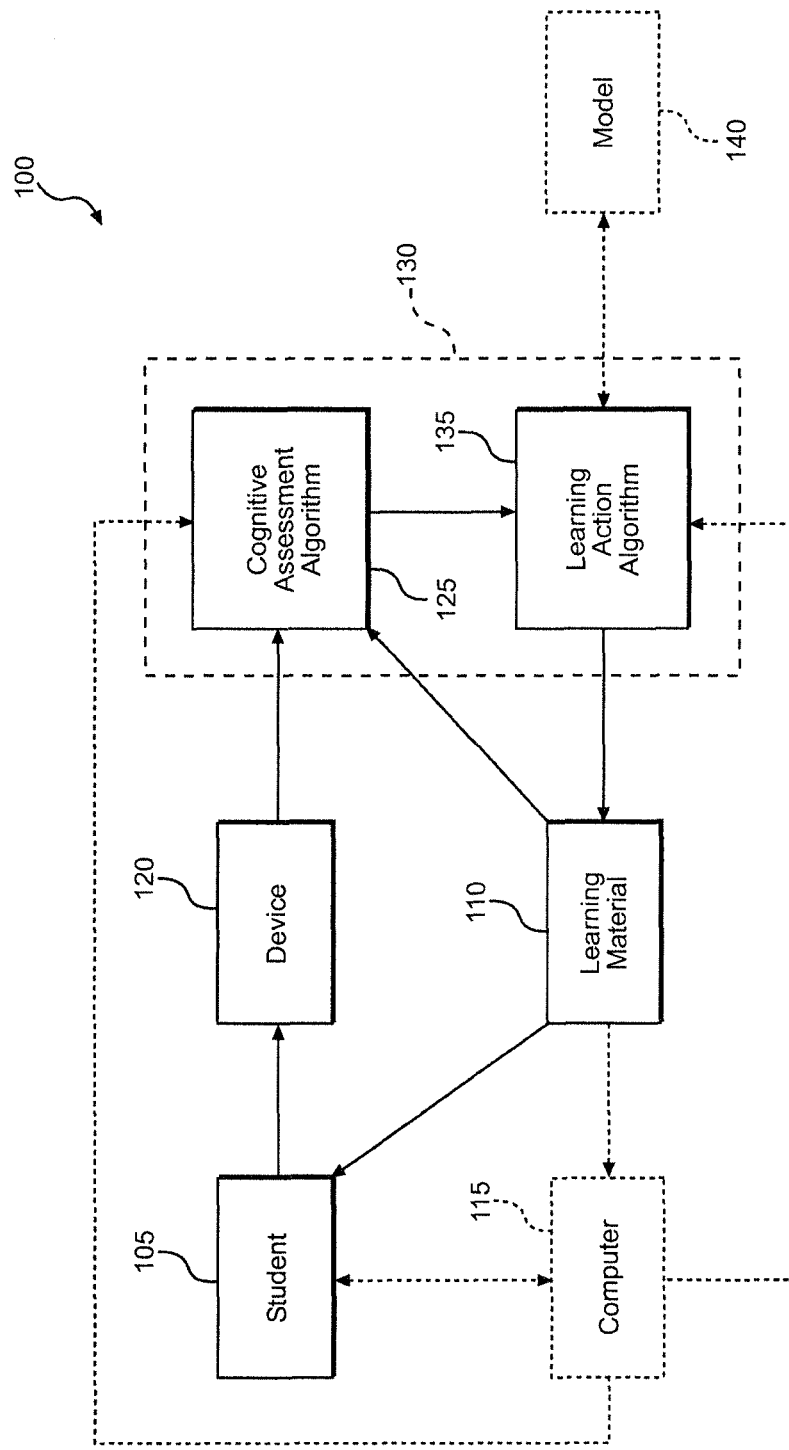
FIG. 1 is a schematic view of a system for improving learning in accordance with the present invention.

With initial reference to FIG. 1, there is shown a schematic view of a system 100 for improving learning in accordance with the present invention. A student 105 interacts with learning material 110, either through a tutor (not shown) or through a computer 115. Learning material 110 generally includes the type of material typically presented to a student in a learning environment, such as lectures, questions, problems or activities, although learning material 110 is not limited to such material. Preferably, computer 115 includes a display for displaying the learning material to the student and an input device that allows the student to interact with computer 115. A device 120 is connected to student 105, and device 120 is configured to measure the student's physiological data. In one embodiment, device 120 is configured to directly measure the brain activity of student 105. Device 120, as detailed further below, passes this data to a cognitive assessment algorithm 125, which can reside in a controller 130 (or a control system), for example. Cognitive assessment algorithm 125 uses the physiological data to determine one or more cognitive states of student 105, such as cognitive load, engagement or fatigue. Cognitive assessment algorithm 125 can also use a response time of student 105 (e.g., from computer 115) or a quantification of a difficulty of learning material 110 in order to determine the cognitive state of student 105.

Information about the cognitive state(s) of student 105 is passed to a learning action algorithm 135, which uses the information in order to modify, in real time, the presentation of learning material 110 to student 105. Learning action algorithm 135 can also use information regarding whether student 105 correctly answered a question or correctly completed a task (e.g., from computer 115) in order to modify the presentation of learning material 110. Such modifications can involve a variety of different changes, including, but not limited to: changing the difficulty or interactivity of subsequent content; providing feedback to student 105; changing the complexity or rate of delivery of learning material 110; providing phrases to praise, motivate, admonish or engage student 105; allowing student 105 to choose additional or alternative content; providing a prompt to induce student 105 to consider the student's reasoning; or adding additional tasks, removing tasks, changing the order of tasks or modifying tasks. In one embodiment, learning action algorithm 135 modifies the presentation of learning material 110 during a lecturing or scaffolding phase of a learning session. Additionally, learning action algorithm 135 can optionally update a model 140 that describes how student 105 learns. As a result, model 140 enables learning action algorithm 135 to more effectively present learning material 110 to student 105 in subsequent learning sessions. As with cognitive assessment algorithm 125, learning action algorithm 135 can be located in controller 130. However, algorithms 125 and 135 need not be located in the same controller. Additionally, when computer 115 is provided, algorithms 125 and 135 can be located within computer 115. Similarly, model 140 can be implemented in controller 130, a separate controller or computer 115.

Figure 2:
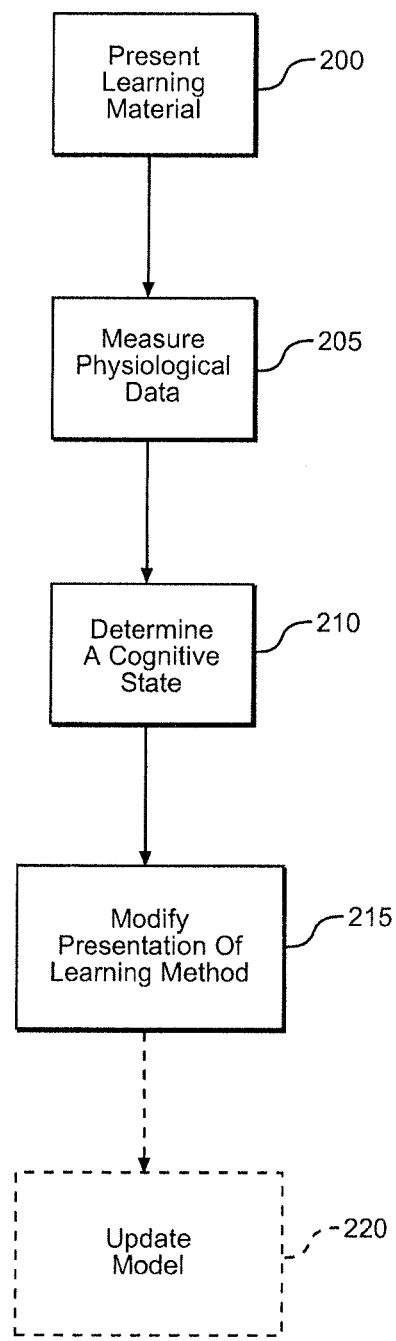
FIG. 2 is a flowchart illustrating a method for improving learning in accordance with the present invention.

FIG. 2 provides a flowchart that illustrates the steps followed by system 100. Initially, at step 200, learning material 110 is presented to student 105, either by a tutor or by computer 115. Next, at step 205, device 120 measures the student's physiological data and passes this data to cognitive assessment algorithm 125. At step 210, cognitive assessment algorithm 125 determines the student's cognitive state and passes this information to learning action algorithm 135. As a result, learning action algorithm 135 modifies the presentation of learning material 110 to student 105 at step 215. Optionally, at step 220, learning action algorithm 135 then updates model 140. Further details regarding system 100, and its associated methods, are provided below.

System Element 1—Learning Material

Learning material generally encompasses the traditional subject content of the source material that is to be learned by the student as well as background material, prompts, encouragement, corrections and other inputs given to the student during the learning session with the goal of supporting the student's learning. As used herein, a learning session is a period of learning during which an amount of learning material is presented to a student, wherein that amount can typically be absorbed by a student in one continuous presentation, without restarting the session.

A good example of the range of learning material envisioned by the invention is that delivered by GURU, an intelligent tutoring system developed at the University of Memphis that uses an animated agent to have conversations with students and interact with graphical illustrations. This system is generally concerned with a computer-based natural language platform which relies on the dialog commonly used by expert human tutors during learning sessions with students. The process flow that GURU follows to deliver content is as follows: a) an introduction that relates the content to the student; b) a lecturing period of information delivery that is interspersed with simple assessments of understanding; c) a scaffolding section that includes several cycles in which GURU asks questions of the student to assess their level of comprehension along with more specific and guided follow-up questions and potentially additional lecturing based on the student's answers to ensure that they have adequately learned the material; and d) interspersed throughout and after the scaffolding session are multiple other activities including summarizing statements, concept maps and other tests of comprehension and learning.

As expected, expert human tutors generally follow the same basic process to deliver content as GURU. However, expert tutors are not always capable of following the same process every time, and not every tutor is an expert tutor. There is a wide variety in the tutoring styles of human tutors, just as there is a wide range in their quality and level of experience. Beyond the scenario followed by GURU and ideal expert tutors to teach a dedicated subject topic, some other scenarios, tactics and activities include: guiding a student through an assigned problem, project or report; leveraging prior learned content from one subject and applying it to a different subject; selecting from among several activities based on the tutor's assessment of a student's level of interest; re-teaching content that was not correctly learned with a different example or set of terminology; and allowing a student to guide the specific questions and topics they need help with. Tutoring sessions can also be accomplished across multiple delivery formats, including individual one-on-one tutoring sessions, small-group sessions with four to eight students or larger-group sessions that are more similar to the school classroom format. Additionally, these sessions can be delivered either online or in-person at a dedicated facility, at the student's home or any other agreed-upon place.

The present invention can be used as an aid to a human teacher in a classroom setting, to a human tutor in a one-on-one setting or directly to a student without guidance from a human instructor. There is no limitation on the type of teaching materials used, provided the cognitive gauges can be used at the same time. With the advent of low cost portable computers and mobile devices, computer based teaching (CBT) systems are now being adopted. Initially, CBT systems simply served to store and present material as if they were electronic books. However, a new generation of adaptive CBT systems decides the presentation of the teaching material based on direct input from the student, either via a questionnaire or indirectly by monitoring the response of the student to problems presented during the learning session.

One particular problem with present CBT systems is that they cannot distinguish whether a student answered a problem incorrectly because the student did not know an answer or because the student was not paying attention. Similarly, present systems cannot distinguish whether a correctly answered problem was very difficult for the student or very easy or in between. Human tutors consciously or unconsciously decide whether a student is making an effort to study and factor this into their impression of the student and decisions about how to present the material. However, such human assessments have varying levels of objectivity and are affected by the workload and emotional state of the tutor.

System Element 2—Physiological Data Measurement

The physiological state of the student can be measured using a device that incorporates one or more of the following technologies:

1) Electroencephalography (EEG): spatially- and temporally-resolved probe of brain electrical activity resulting from spontaneous neuron activation. Voltage fluctuations are measured at multiple sites on the scalp using electrodes that make resistive or capacitive contact to the subject. Example brain signals are EEG data, event-related potentials (ERP) and other brain electrical responses that are manifest in the time and/or frequency domain.

2) Functional near-infrared spectroscopy (fNIR): probe of hemodynamic changes in the brain and scalp tissue. A measurement of optical attenuation on the scalp is used to quantify the relative and absolute chromophore concentration. Oxygenation and deoxygenation of the hemoglobin in brain tissue is associated with localized neuron activation as well as global hemodynamic changes resulting from cyclical and noncyclical changes in arterial blood pressure.

3) Functional magnetic resonance imaging (fMRI): probe of hemodynamic changes in the brain associated with neuron activation. A measurement of the localized magnetization of brain tissue is used to quantify the relative and absolute changes in oxygenated and deoxygenated blood concentration.

4) Magnetoencephalography (MEG): spatially- and temporally-resolved probe of brain electrical activity resulting from spontaneous neuron activation. Fluctuations in the magnetic field are measured at multiple sites on the scalp using multiple magnetometers.

5) Electrocorticography (ECoG): spatially- and temporally-resolved probe of brain electrical activity resulting from spontaneous neuron activation. Voltage fluctuations are measured at multiple sites on the scalp using subcranial electrodes.

6) Electrocardiography (ECG): probe of the electrical activity of the heart, measured using multiple electrodes making resistive or capacitive contact to the skin. ECG is processed in the time and frequency domains. Heart-rate variability (HRV) metrics are also extracted.

7) Galvanic skin response (GSR): measurement of the electrical conductance of the skin regulated by the sympathetic nervous system.

8) Eye tracking: measurement of the eye motion, point of gaze or blink metrics of the subject.

9) Facial recognition: measurement of the facial features of the subject that relate to fatigue, emotion and cognitive state.

10) Posture and gesture recognition: measurement of the subject's posture and gestures, including sitting position, leaning angle, weight distribution, hand position and gestures.

11) Input metrics: metrics gathered from keystroke, mouse or other related computer input methods including keystroke response time, mouse movement range and speed.

The EEG can be measured by a number of available commercial recording systems. Electrodes are held against the scalp at desired positions on the head. An electrically conducting fluid is used to couple the electrical signal on the scalp into the first stage amplifiers of the recording system. Recently, an EEG recording system that does not require the use of any fluids on the scalp has been introduced. Such a system is particularly advantageous for use with the invention because of reduced set up time and the absence of fluid residue in the hair after its use.

System Element 3—Cognitive State Determination

As discussed above, the electroencephalogram (EEG) is a measure of the electrical activity of the brain in the vicinity of the measurement region. In the last five years, EEG has been successfully related in real time to a number of cognitive states, including cognitive workload, attention and fatigue. Broadly speaking, the cognitive state is deduced while a subject engages in a particular cognitive activity expected to result in that state (e.g., mental arithmetic) while the EEG is recorded. Mathematical algorithms are able to correlate the measured EEG data to the cognitive state present so that this state can be identified in EEG recordings of a subject. See, for example, Matthews, R. et al., "Real Time Workload Classification from an Ambulatory Wireless EEG System Using Hybrid EEG Electrodes", 30th Annual International IEEE EMBS Conference, Vancouver, Canada. (2008); McDonald, N. J. et al., "QUASAR's QStates Cognitive Gauge Performance in the Cognitive State Assessment Competition 2011" 33rd Annual International Conference of the IEEE EMBS. Boston, Mass. August 2011, pp. 6542-6; and Soussou, W. et al., "EEG and Eye-Tracking Based Measures for Enhanced Training" 34th Annual International Conference of the IEEE EMBS. August 2012, 1623-6 incorporated herein by reference in their entirety. The mathematical algorithm that converts the raw EEG data to a quantification of a particular mental state is commonly referred to as a cognitive gauge. The step of determining the internal coefficients of the algorithm for a given cognitive state is known as training the algorithm.

EEG cognitive gauges can now provide an accurate quantification of cognitive engagement and cognitive load while a student is performing intellectual tasks such mental arithmetic. Gauges can be trained for other cognitive states, such as fatigue, boredom, frustration or mind-wandering, by inducing such states in the subject while EEG is recorded. The output of one or more gauges can be used to directly inform a teacher about a student's mental state. For example, a gauge could inform a human tutor that a student is in a state of low engagement with the subject matter. The tutor could choose to ignore this information or consider it an aspect of the student to take into consideration.

The student's cognitive state is determined from the physiological data measured by the device described above in connection with a cognitive assessment algorithm. A cognitive assessment algorithm provides near real-time classification of cognitive state or mental load based on data collected during cognitive-specific tasks. The cognitive assessment algorithm handles any source physiological data specified in connection with the device of System Element 2 as inputs, and derives cognitive state gauges whose numerical value corresponds to a measure of the cognitive state being classified.

The cognitive assessment algorithm appropriately preprocesses each signal source and extracts an array of features, which are computed for an epoch of the dataset, typically one to two seconds in duration. The features are combined with ground truths of the cognitive state and used as inputs to train a cognitive model, through Partial Least Squares or other machine learning algorithms. The model establishes the relationship between input and output variables while maintaining most of the input variables' information. Features extracted from the physiological data are likewise used to classify a cognitive state using an existing model. Efficient pre-processing and classification algorithms can enable rapid offline training of models and near real-time classification of physiological data. Models constructed by cognitive assessment algorithms can be specific to individual subjects and tasks, or allows for crosspollination and generalization across multiple subjects.

Cognitive assessment algorithms have been used to classify cognitive engagement and cognitive workload of subjects engaged in a first person shooting game, in simulated unmanned aerial vehicle (UAV) control missions and in X-ray screening simulation tasks. Classification accuracies averaged across subjects performing these tasks have consistently produced better than 90% accuracies on two-state classification for both engagement and workload.

System Element 4—Modifying Learning Material Presentation—The Learning Action Algorithm In the simplest embodiment of the invention, a cognitive gauge or could be used as a real time input to an adaptive teaching program. In another embodiment, the output of two or more cognitive gauges could be used. In a further embodiment, the output of one or more cognitive gauges can be combined with one or more measures of the high level response of the student to the learning experience. In a yet further embodiment, the output of one or more cognitive gauges, one or more measures of the high level response of the student to the learning experience are combined with outputs from the student's learning model which tracks the student's learning progress and metrics across lessons. In all cases, we term the component of the system that takes such inputs the learning action algorithm. The output of the learning action algorithm is a control signal that is used to modify the learning material. Such modifications can include one or more of the following:

1) Modifying the difficulty of instruction. For example, the learning action algorithm can: modify the complexity of the textual information by varying sentence length, word frequency, syntactic complexity, cohesion and narrativity; or modify the number and level of hints presented during instruction, accompanying either the textual, visual or auditory content.

2) Modifying the difficulty of evaluation, principally through the number and level of hints presented during scaffolding and other learning modes.

3) Modifying the speed or style (such as visual, verbal, auditory, interactive or other presentation styles) of content delivery.

4) Modifying the order and duration of learning modes such as instruction, evaluation and scaffolding.

5) Inserting additional individualized tasks. In general, a curriculum is comprised of a series of learning items that are arranged in a scripted manner. Examples of an individualized task that could be inserted into a curriculum are: reading an additional section of text; doing a virtual laboratory experiment; or solving a problem. Such an individualized task is generally a multi-minute, multistep activity.

6) Inserting a prompt into the dialog for the student to explain their reasoning. It is common for students to embark on a line of reasoning when tackling a problem, or follow a complex explanation, and get stuck. A prompt to explain reasoning can redirect them to address a fundamental error in their understanding or approach.

7) Allowing the student to modify the content. For example, the student can be asked if he would like to receive some historical background or hear an explanation from the perspective of another person in a dialog or in a more or less mathematically complex way.

8) Inserting praise or motivational phrases.

9) Adding background domain knowledge. Possible examples include: anecdotes that demonstrate the relative importance of a given subtopic within the larger course; an associated historical fact; or a common example of the same phenomenon.

10) Adding a phrase to reengage the student's attention. Candidate phrases include: admonitions (e.g., "please try harder", "look this way"); a reference to how far the student has progressed (e.g., "over half way"); and sudden sounds or visual effects.

11) Inserting a pause or brief game to provide time to refocus attention.

These modifications can be applied at any time during the learning session, but a particularly effective time is during periods when the student's reasoning is being scaffolded. Scaffolding is a kind of guided prompting that pushes students a little further along the same line of thinking. The goal of scaffolding is to extend the student's reasoning, and, thus, it is a critical part of many learning sessions.

Table 1 provides examples of scenarios in which the learning content modifications 1-11, described above, would be activated by one or more specific cognitive states (determined by the cognitive assessment algorithm) and/or one or more high level responses (i.e., the learning action algorithm). As a specific example, the high level response of the student in Table 1 could be the time taken to activate the system to continue (e.g., click a mouse or scroll down a screen).

TABLE I

Examples of a Learning Action Algorithm Outputs Implemented for Cognitive States Including Workload, and Cognitive Engagement and the Response of Student Progression Rate.

| Change/Addition to learning content | Triggering cognitive state(s) and or responses that might activate the change/addition | Model of student response to learning material |
| --- | --- | --- |
| a. Individualized tasks | High workload, slow response to current content | Lacking understanding |
| b. Explain reasoning | Low workload, high engagement, slow response to current content | Incorrect understanding |
| c. Student content modification | Low engagement, fast response to current content | Losing interest |
| d. Praise | High workload, high engagement | Working hard |
| e. Add background knowledge | Low engagement, slow response to current content | Losing interest, but finding material challenging |
| f. Engaging phrase | Low engagement, no response to current content | Stopped working |
| g. Pause, insert game | High workload, slowing over recent content | Tired, need refreshment |
| h. Increase language complexity | Low workload, high engagement, fast response | Has capacity/desire to learn more comprehensively |
| i. Increase rate of delivery | Low workload, low engagement | Presentation too slow for student |

The learning action algorithm can be implemented as a simple logical mapping, or via algebraic formulae. In one embodiment, a learning action algorithm takes a simple binary (high/low) quantification of engagement and cognitive load and a simple binary quantification of the student response to a problem posed (right/wrong) and produces an instruction to modify the difficulty of the next content presented to the student. An example of possible learning action algorithm outputs for the eight combinations of binary inputs for engagement and cognitive load and student response are shown in Table 2. A mapping of the same variables to adjust the interactivity level of a CBT system is shown in Table 3.

TABLE 2

Example of a Learning Action Algorithm to Map Current States of Engagement and Cognitive Load to the Difficulty Level of the Subsequent Material Presented to the Student.

| Current Content | | | Next Content |
|---|---|---|---|
| Engagement | Cognitive Load | Response | Difficulty |
| High | High | Right | Keep the Same |
| High | High | Wrong | Reduce |
| High | Low | Right | Increase |
| High | Low | Wrong | Keep the Same |
| Low | High | Right | Increase |
| Low | High | Wrong | Reduce |
| Low | Low | Right | Increase |
| Low | Low | Wrong | Take a Break, Stop |

TABLE 3

Example of a Learning Action Algorithm to Map Current States of Engagement and Cognitive Load to the Interactivity Level of the Subsequent Material Presented to the Student.

| Current Content | | | Next Content |
|---|---|---|---|
| Engagement | Cognitive Load | Response | Interactivity |
| High | High | Right | Keep the Same |
| High | High | Wrong | Keep the Same |
| High | Low | Right | Keep the Same |
| High | Low | Wrong | Keep the Same |
| Low | High | Right | Increase |
| Low | High | Wrong | Increase |
| Low | Low | Right | Increase |
| Low | Low | Wrong | Take a Break, Stop |

In the learning action algorithms illustrated in Tables 1, 2 and 3, the high level response of the student to the learning experience is the speed of the student response and whether the student answered a question about the teaching material correctly. Another high level response would be how the student assesses the difficulty of the material (e.g., easy, medium, or hard). Yet another high level response would be the time to respond to a particular question or complete a section of teaching material. There are many possible high level responses depending on the profile of the student and learning material, and the learning action algorithm is not restricted to any one response of combination of responses.

The learning action algorithm can be a mathematical algorithm with a deterministic output. Although Tables 2 and 3 illustrate how a learning action algorithm maps binary states of engagement, cognitive load and response to levels of difficulty and interactivity, a learning action algorithm is not limited to only binary inputs. For example, multiple discrete levels of cognitive load or engagement could be identified, as in the work of Matthews, R. et al., "Real Time Workload Classification from an Ambulatory Wireless EEG System Using Hybrid EEG Electrodes", 30th Annual International IEEE EMBS Conference, Vancouver, Canada. (2008); McDonald, N. J. et al., "QUASAR'S QStates Cognitive Gauge Performance in the Cognitive State Assessment Competition 2011" 33rd Annual International Conference of the IEEE EMBS. Boston, Massa. August 2011, pp. 6542-6; and Soussou, W. et al., "EEG and Eye-Tracking Based Measures for Enhanced Training" 34th Annual International Conference of the IEEE EMBS. August 2012, 1623-6. Similarly, an input such as cognitive load could range continuously, for example from 0 to 1 with 1 representing the highest possible state of cognitive load. Furthermore, the output of a learning action algorithm is not limited to a single variable, such as difficulty or interactivity as illustrated in Tables 2 and 3, but can provide multiple outputs. For example, a learning action algorithm can produce outputs to affect both difficulty and interactivity, as illustrated in Table 4.

TABLE 4

Example of a Learning Action Algorithm to Map Current States of Engagement and Cognitive Load to the Difficulty and Interactivity Level of the Subsequent Material Presented to the Student.

| Current Content | | | Next Content | |
|---|---|---|---|---|
| Engagement | Cognitive Load | Response | Difficulty | Interactivity |
| High | High | Right | Keep the Same | Keep the Same |
| High | High | Wrong | Reduce | Keep the Same |
| High | Low | Right | Increase | Keep the Same |
| High | Low | Wrong | Keep the Same | Keep the Same |
| Low | High | Right | Keep the Same | Increase |
| Low | High | Wrong | Reduce | Increase |
| Low | Low | Right | Increase | Keep the Same |
| Low | Low | Wrong | Take a Break, Stop | Take a Break, Stop |

The output of the learning action algorithm can be presented to a teacher or used as an input to a CBT program to guide the content of the next material presented to the student. For an adaptive CBT program, the learning action algorithm output provides a real time recommendation of how to adjust the program to best adapt to the student. In some cases, the learning action algorithm can be used as the only real time input to modify the CBT content presented to the student. Regardless of how the output of the learning action algorithm is used and the number of variables in its output, we term the learning action algorithm output to be a teaching output.

As illustrated in Tables 2-4, the output of the cognitive gauges can be stratified into discrete levels (e.g., high and low) or be a continuous parameter. Further, the outputs of the cognitive gauges can be combined with further physiologic measures of the student to give a more complete assessment of the student's cognitive response to the teaching material being presented. For example, the time it takes the student to read the material, the response time to a request or question posed, the total time the student has been engaged in learning, or the position of his/her gaze and posture in the chair are all variables that can be measured. Further, information related to the material itself, such as the difficulty of the teaching material and the target age range of the material, can be included. For convenience, we term an algorithm that combines gauges determined from EEG data with simultaneous physiologic measures of the student in order to produce a more complete measure of the student's cognitive response to the presented material to be a cognitive assessment algorithm, as described above.

The cognitive assessment algorithm augments the EEG-derived cognitive gauge outputs to produce a more complete picture of the student's cognitive state. For example, cognitive load can be augmented with one or more physiologic and material content measures to give a metric of student effort. Similarly, engagement can be augmented to give a measure of student focus. Table 5 illustrates a cognitive assessment algorithm that combines binary measures of cognitive load, response time and task difficulty to produce a three-level quantification of student effort.

TABLE 5

Example of a Cognitive Assessment Algorithm to Map Current States of Cognitive Load, Response Time, and Task Difficulty to Student Effort.

| Cognitive Load | Response Time | Task Difficulty | Student Effort |
| --- | --- | --- | --- |
| High | Short | High | High |
| High | Long | High | High |
| Low | Short | High | High |
| Low | Long | High | Medium |
| High | Short | Low | Medium |
| High | Long | Low | Medium |
| Low | Short | Low | Low |
| Low | Long | Low | Low |

The learning action algorithm can be implemented in different ways and can be modified in an adaptive manner during a learning session based on the individual student responses. A key aspect of the learning action algorithm, as envisioned herein, is that it can operate in real time on all types of learning material, rather than requiring content-related questions to be answered. By real time it is meant that the acquisition of the cognitive data, the updating of the output of the cognitive assessment algorithm, the processing by the learning action algorithm and the subsequent modification of the learning content occur within the natural timescale of the learning material, so that the modifications can beneficially support the student.

Furthermore, the identity, frequency and change of models identified during the learning session and the student's response to the modification of the learning material can be treated as inputs into a comprehensive learner model that spans multiple sessions. For example, using the models in Table 1, identifying that a student routinely enters the "Tired, need refreshment" model after about 35 minutes of a lesson can allow the tutoring system to automatically adjust the teaching approach so that the lessons are no longer than 35 minutes. In another example, the system can identify that the student regularly enters the model "Losing interest but finding material challenging" during specific activities (i.e., those that are uninteresting), but not others (i.e., those that are interesting). The system would then, for this specific student, de-emphasize the use of certain uninteresting activities and emphasize the use of the more engaging activities in future lessons.

Further, the learning action algorithm can include updating or otherwise revising a model of the student's learning style as it varies with time throughout and across learning sessions in response to the particular material that is present. In contrast to prior methods of constructing a predictive student model or models, when used in this mode, the learning action algorithm provides both real time updates to the model and context specific updates that are related directly to the material being presented and the individual subject. For example, the learning action algorithm can take into account the cognitive response of the student to audio vs. visual stimuli during different stages of the learning process.

Based on the above, it should be readily apparent that the present invention provides systems and methods for improving student learning by determining a student cognitive state and modifying the presentation of learning material in real time. Although described with reference to preferred embodiments, it should be readily understood that various changes or modifications could be made to the invention without departing from the spirit thereof. For example, other technologies can be used to determine a cognitive state of a student. Additionally, the algorithms and model can be implemented in various different computer systems. In general, the invention is only intended to be limited by the scope of the following claims.

The invention claimed is:

1. A system for improving student learning comprising:
   learning material having content for presentation to a student;
   an EEG system configured to measure a cognitive load of the student as the learning material is presented in a learning session;
   a device configured to measure physiological data of the student as the learning material is presented in the learning session, wherein the data includes at least three of a brain activity of the student, a measurement of the time it takes the student to read the material, a response time of the student to a request or question posed, a correctness of a response by the student, a total time the student has been engaged in learning, a position of gaze of the student and a posture of the student;
   a cognitive assessment algorithm configured to determine a cognitive state of the student based on the cognitive load and the physiological data; and
   a learning action algorithm configured to modify a continued presentation of the learning material in real time based on the cognitive state of the student.

2. The system of claim 1, wherein the device is configured to directly measure the brain activity of the student, with the data further including, in combination with the brain activity, the correctness of the response by the student and at least one of the measurement of the time it takes the student to read the material, the response time of the student to the request or question posed, the total time the student has been engaged in learning, the position of gaze of the student and the posture of the student.

3. The system of claim 2, wherein the device includes an eye-tracking system and the data includes the position of gaze of the student during the presentation of material and at least one of the measurement of the time it takes the student to read the material, the response time of the student to the request or question posed, and the total time the student has been engaged in learning.

4. The system of claim 1, wherein the cognitive state is the student's cognitive load or fatigue.

5. The system of claim 1, further comprising:
   a computer system including a display for displaying the learning material to the student and an input device for receiving input from the student and wherein the cognitive state of the student is represented by a binary variable.

6. The system of claim 1, wherein the data includes each of the brain activity of the student, the correctness of the response by the student, the measurement of the time it takes the student to read the material, the response time of the student to the request or question posed, the total time the student has been engaged in learning, the position of gaze of the student and the posture of the student.

7. A method for improving student learning, the method comprising:
   presenting learning material to a student;
   measuring physiological data of the student with a device as the learning material is presented, wherein the data includes at least three of a brain activity of the student, a measurement of the time it takes the student to read the material, a response time of the student to a request or question posed, a correctness of a response by the student, a total time the student has been engaged in learning, a position of gaze of the student and a posture of the student;

determining a cognitive state of the student with a cognitive assessment algorithm that uses the physiological data; and modifying a continued presentation of the learning material in real time with a learning action algorithm that uses the cognitive state of the student.

8. The method of claim 7, wherein presenting the learning material to the student includes lecturing the student; asking the student questions; or providing the student with problems or activities to complete.

9. The method of claim 7, wherein measuring the physiological data of the student includes directly measuring the brain activity of the student and one or more of the following:

ECG or HRV of the student; and
GSR of the student.

10. The method of claim 7, wherein determining the cognitive state of the student includes determining the student's cognitive load or fatigue.

11. The method of claim 10, wherein determining the cognitive state of the student includes determining the student's fatigue.

12. The method of claim 7, wherein modifying the presentation of the learning material includes:

changing the difficulty or interactivity of subsequent learning material;

changing the complexity or rate of delivery of the learning material;

changing a delivery style of the learning material;

allowing the student to choose additional or alternative learning material;

or adding additional learning material, removing learning material, changing the order of the learning material or modifying the learning material.

13. The method of claim 7, wherein modifying the presentation of the learning material includes changing an interactivity of subsequent learning material.

14. The method of claim 7, wherein modifying the presentation of the learning material includes allowing the student to choose additional or alternative learning material.

15. The method of claim 7, wherein modifying the presentation of the learning material includes changing the order of the learning material.

16. The method of claim 7, wherein presenting the learning material to the student includes displaying the learning material on a display of a computer system, and wherein the method further comprises reducing the cognitive state of the student to a binary variable.

17. The method of claim 7, further comprising:

updating a model of the student that describes how the student learns.

18. The method of claim 7, wherein the learning action algorithm also uses a quantification of a difficulty of the learning material in order to determine the cognitive state of the student.

19. The method of claim 7, wherein measuring the physiological data of the student includes the brain activity of the student, the correctness of the response by the student and at least one of the measurement of the time it takes the student to read the material, the response time of the student to the request or question posed, the total time the student has been engaged in learning, the position of gaze of the student and the posture of the student.

20. The method of claim 19, wherein measuring the physiological data of the student includes each of the brain activity of the student, the correctness of the response by the student, the measurement of the time it takes the student to read the material, the response time of the student to the request or question posed, the total time the student has been engaged in learning, the position of gaze of the student and the posture of the student.

* * * * *